(12) United States Patent
Ahn et al.

(10) Patent No.: US 11,627,880 B2
(45) Date of Patent: *Apr. 18, 2023

(54) REAL-TIME PARATHYROID IMAGING SYSTEM

(71) Applicants: PUKYONG NATIONAL UNIVERSITY INDUSTRYUNIVERSITY COOPERATION FOUNDATION, Busan (KR); UNIST (ULSAN NATIONAL INSTITUTE OF SCIENCE AND TECHNOLOGY), Ulsan (KR)

(72) Inventors: Yeh-Chan Ahn, Busan (KR); Sung Chul Bae, Ulsan (KR)

(73) Assignees: PUKYONG NATIONAL UNIVERSITY INDUSTRYUNIVERSITY COOPERATION FOUNDATION, Busan (KR); UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 255 days.

This patent is subject to a terminal disclaimer.

(21) Appl. No.: 16/764,539

(22) PCT Filed: Nov. 5, 2018

(86) PCT No.: PCT/KR2018/013287
§ 371 (c)(1),
(2) Date: May 15, 2020

(87) PCT Pub. No.: WO2019/098581
PCT Pub. Date: May 23, 2019

(65) Prior Publication Data
US 2020/0281475 A1    Sep. 10, 2020

(30) Foreign Application Priority Data

Nov. 17, 2017   (KR) .................... 10-2017-0154266

(51) Int. Cl.
*A61B 5/00* (2006.01)
(52) U.S. Cl.
CPC .......... *A61B 5/0082* (2013.01); *A61B 5/0071* (2013.01); *A61B 5/0077* (2013.01); *A61B 5/4227* (2013.01); *A61B 2562/0233* (2013.01)

(58) Field of Classification Search
None
See application file for complete search history.

(56) References Cited

U.S. PATENT DOCUMENTS

| 2010/0036203 | A1  | 2/2010 | Nakaoka et al. |
| 2013/0096392 | A1* | 4/2013 | Adams ............... A61B 5/14546 600/301 |

(Continued)

FOREIGN PATENT DOCUMENTS

| EP | 2283766 A1     | 2/2011 |
| KR | 1020140101930 A | 8/2014 |
| KR | 1920160008196 A | 1/2016 |

OTHER PUBLICATIONS

European Search Report (In English), dated Jun. 28, 2021, of European Patent Application No. EP 18 87 9050.5, EP National Stage of International Application PCT/KR2018/013287, filing date Nov. 5, 2018.

(Continued)

*Primary Examiner* — Shahdeep Mohammed
(74) *Attorney, Agent, or Firm* — Barcelo, Harrison & Walker, LLP

(57) ABSTRACT

The present invention relates to a real-time parathyroid imaging apparatus including: a light source including an excitation filter capable of exciting parathyroid glands; and (Continued)

a camera including an image sensor and an emission filter of which a transmissivity ratio between a visible light region and a near-infrared emission wavelength region is N:1 (here, N<1). Through the present invention, a system may be implemented whereby a surgeon may acquire, in real-time during an operation, an autofluorescence image of the parathyroid glands by using a near-infrared light source, and an auto focus function may be used, and visible light and near-infrared autofluorescence images may be simultaneously fused and acquired without having to turn off the lights in an operating room.

4 Claims, 9 Drawing Sheets

(56) References Cited

U.S. PATENT DOCUMENTS

| | | |
|---|---|---|
| 2015/0182118 A1 | 7/2015 | Bradbury et al. |
| 2016/0356720 A1* | 12/2016 | Van Dorpe .......... G02B 6/0026 |
| 2017/0046586 A1 | 2/2017 | Abbas et al. |
| 2017/0105623 A1 | 4/2017 | Mahadevan-Jansen et al. |
| 2017/0209050 A1 | 7/2017 | Fengler et al. |
| 2017/0236022 A1 | 8/2017 | Abbas et al. |

OTHER PUBLICATIONS

Korean Patent Abstract (in English) of Korean Patent App. Pub. No. KR10-2014-0101930 A, Pub. dated Aug. 21, 2014, downloaded Jan. 26, 2021, from https://worldwide.espacenet.com.

Korean Patent Abstract (in Korean) of Korean Patent App. Pub. No. KR10-2016-0008196 A, Pub. dated Jan. 21, 2016, downloaded Jan. 26, 2021, from https://worldwide.espacenet.com.

Non-Patent Literature Document in Korean "Intraoperative localizing of parathyroid glands using near-infrared autofluorescence imaging", authors: Yeh-Chan Ahn, Seo Hyun Song, Sung Won Kim, Hyoung Shin Lee, Chulho Oak, Kang Dae Lee, dated: Nov. 22, 2015, publisher: The Korean Society of Mechanical Engineers, pp. 2235 to 2237.

* cited by examiner (a)

(b)

(a)

(b)

(c)

REAL-TIME PARATHYROID IMAGING SYSTEM

CROSS-REFERENCE TO RELATED APPLICATIONS

This application is the national stage of International Patent Cooperation Treaty Application PCT/KR2018/013287 filed 5 Nov. 2018, which claims priority from Korean Patent Application No. 10-2017-0154266 filed 17 Nov. 2017, in the Korean Intellectual Property Office. The entire contents of said applications are incorporated herein by reference for all purposes.

BACKGROUND

Technical Field

The present invention relates to a real-time parathyroid imaging system, and particularly, to an imaging system capable of acquiring an autofluorescence image of a parathyroid by using a near-infrared light source in real time.

Background Art

In thyroid dissection for removing thyroid tumors, it is very important to preserve parathyroid for maintaining calcium homeostasis of our body. Since the parathyroid is a very small and delicate organ having a weight of 35 to 45 mg and a size of approximately 5×3×1 mm, it is not easy to distinguish the parathyroid from surrounding tissues such as thyroid and a lymph gland with the naked eyes.

FIG. 1(a) illustrates a location of parathyroid and FIG. 1(b) illustrates lymph node subgroups of the neck separated into levels relevant for surgical dissections.

Referring to FIG. 1(a), it can be seen that the parathyroid is positioned at a rear side of thyroid positioned at the center of a front of a neck. There are generally a total of 4 parathyroids, and one is positioned at each of left upper and lower portions and one is positioned at each of right upper and lower portions.

As indicated in FIG. 1(b) illustrating the subgroups of the lymph gland, lymph glands (level VI) surrounding thyroid are dissected together by considering a metastasis possibility at the time of thyroid tumor dissection. This is referred to as central compartment neck dissection (CCND). Dividing the lymph gland into the subgroups according the location is referred to as a level system. The level system is classified into a total of 7 levels. It is characterized in that among 7 levels, the thyroid is present in section level VI and papillary thyroid carcinoma primarily spreads well to lymph gland level VI.

At the time of performing the central compartment neck dissection, since a normal lymph gland is very small, it is almost impossible to identify the normal lymph gland with the naked eyes. Accordingly, both a fatty tissue and a connective tissue including the lymph gland are removed at the time of dissecting the lymph gland.

Here, it becomes important to determine the location of the parathyroid. The reason is that it is not easy to distinguish the parathyroid from the surrounding fatty tissue or connective tissue in section level VI unless a person is a skilled surgeon.

FIG. 2 illustrates a conventional parathyroid imaging system, and FIG. 3(a) is a spectrum graph of an LED light source in which a center wavelength is 780 nm, FIG. 3(b) is a spectrum graph of an excitation filter having a center wavelength of 769 mm and a bandwidth of 41 nm, FIG. 3(c) is a spectrum graph of an emission filter having a center wavelength of 832 mm and a bandwidth of 37 nm, and FIG. 3(d) is a graph showing sensitivity depending on a wavelength of a camera sensor which is a detector, in the conventional parathyroid imaging system according to FIG. 2.

The conventional real-time parathyroid imaging system includes a light source capable of exciting the parathyroid, a camera (or detector) capable of detecting autofluorescence emitted by the parathyroid, and a near-infrared illuminator (IR) allowing the camera to acquire a surrounding image of the parathyroid together in addition to the autofluorescence of the parathyroid by illuminating the vicinity of the parathyroid.

An excitation filter may be included in the light source and an emission filter may be included in the camera.

Since the parathyroid has a particular excitation spectrum and a particular emission spectrum, there should be a light source (FIG. 3(a)) and a camera (FIG. 3(d)) suitable therefor. In this case, since the excitation spectrum and the emission spectrum generally overlap with each other, an appropriate excitation filter (FIG. 3(b)) and an emission filter (FIG. 3(c)) should be used.

In this case, excitation light passing through the excitation filter sufficiently excites the parathyroid and a transmission wavelength band of the excitation filter should be appropriately selected so as to prevent the excitation light from being detected by the camera together with the autofluorescence by passing through even the emission filter and fluorescence emitted from the parathyroid is sufficiently detected by the camera and the transmission wavelength band of the emission filter should also be appropriately selected so as to prevent the excitation light from being detected by the camera.

DISCLOSURE

Technical Problem

An object of the present invention is to provide an imaging system providing convenience of a surgeon during thyroid dissection by using the fact that parathyroid emits stronger autofluorescence than thyroid and surrounding tissues.

Technical Solution

In order to solve the technical problem, a parathyroid imaging system according to the present invention includes: a light source including an excitation filter capable of exciting parathyroid glands; and a camera including an image sensor and an emission filter of which a transmissivity ratio between a visible light region and a near-infrared emission wavelength region is N:1 (here, N<1).

Further, the N is in the range of 0.01 to 0.0001.

Further, the emission filter has an optical density (OD) of an excitation wavelength band of 6 or more in a near-infrared region.

Further, the emission filter is positioned adjacent to the image sensor.

Advantageous Effects

Effects of a real-time parathyroid imaging apparatus according to embodiments of the present invention will be described below.

Through the present invention, a surgeon can acquire an autofluorescence image of parathyroid by using a near-infrared light source in real time during an operation.

Further, a system can be implemented in which an auto focus function can be used and visible light and near-infrared autofluorescence images can be simultaneously fused and acquired without having to turn off lights in an operating room.

Further, a complex multi-channel system can be implemented by one camera without using a plurality of cameras.

However, effects obtainable by a real-time parathyroid imaging system according to embodiments of the present invention are not limited to the aforementioned effects and other unmentioned effects will be clearly understood by those skilled in the art from the following description.

BRIEF DESCRIPTION OF THE DRAWINGS

In order to help understand the present invention, the accompanying drawings which are included as a part of the Detailed Description provide embodiments of the present invention and describe the technical spirit of the present invention together with the Detailed Description.

DETAILED DESCRIPTION

Best Mode

Figure 6:
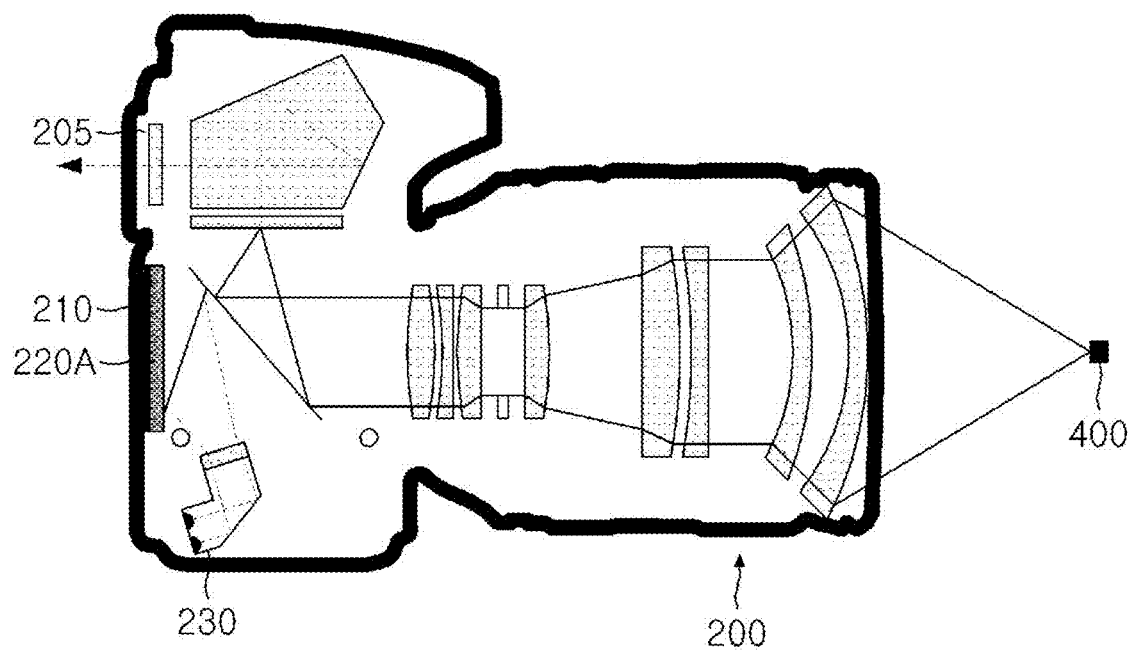
FIG. 6 illustrates a DSLR camera structure with an autofluorescence and visible light emission filter 220A according to the present invention.
Figure 7:
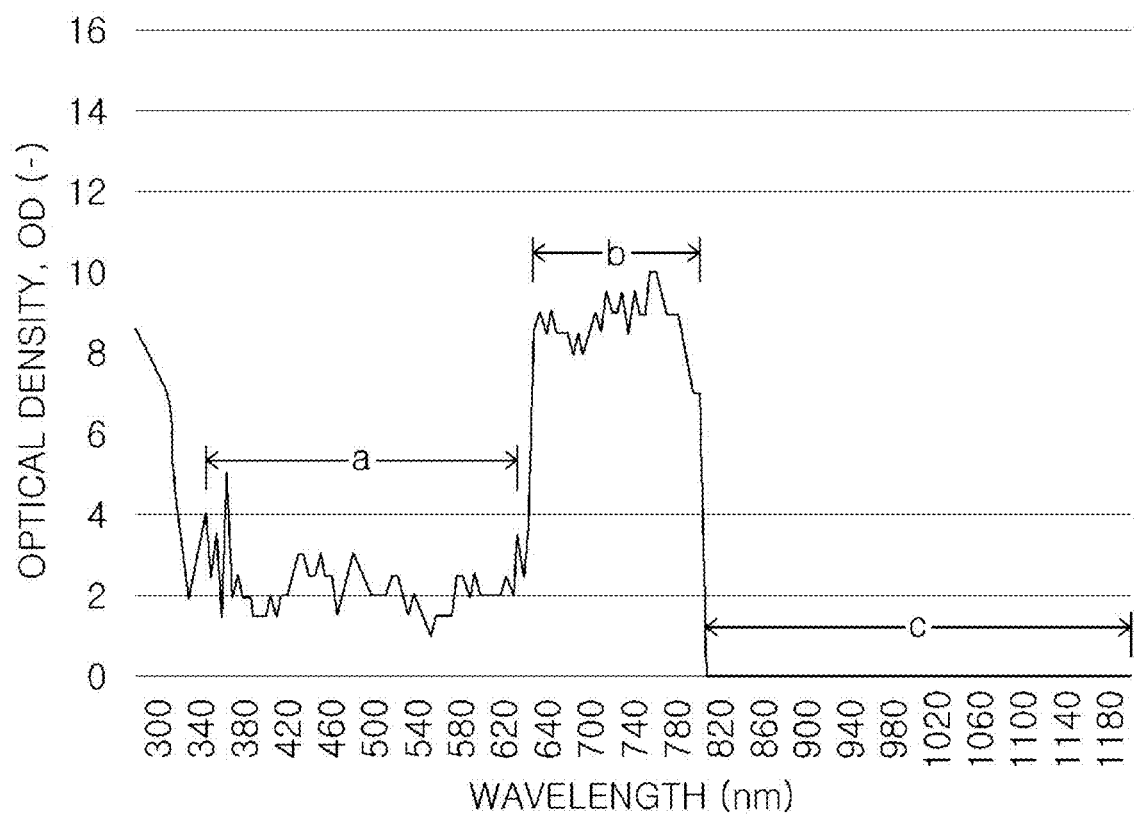
FIG. 7 is a graph showing an optical density (OD) depending on wavelength of the emission filter 220A according to an embodiment of the present invention.

FIG. 6 illustrates a DSLR camera structure with an autofluorescence and visible light emission filter 220A according to the present invention and FIG. 7 is a graph showing an optical density (OD) depending on wavelength of the emission filter 220A according to an embodiment of the present invention.

Only a near-infrared autofluorescence image of the parathyroid may be acquired through the camera illustrated in FIG. 5(a) or 5(b). When using near-infrared illuminator in addition to an excitation light source, it is possible to image not only the parathyroid but also a periphery thereof, but when only the image of the near-infrared region is acquired, it is inconvenient for a surgeon to recognize the location of the parathyroid during an operation due to a significant difference from the image in the visible light region recognized by a person.

In the present invention, in order to supplement the inconvenience, an autofluorescence and visible light emission filter 220A is introduced in the camera, which enables the location of the parathyroid to be recognized in a surrounding structure in an operation room by fusing a near-infrared autofluorescence image and a visible light image into one image.

In FIG. 6, as the camera according to the present invention, a camera can be seen, which includes the autofluorescence and visible light emission filter 220A for acquiring a fused image in addition to an auto focus function.

A transmission spectrum of the autofluorescence and visible light emission filter 220A is adjusted to allow the visible light to pass with a similar intensity as the near-infrared autofluorescence and the autofluorescence and visible light emission filter 220A is installed adjacent immediately in front of the image sensor 210. Since the intensity of the visible light is stronger than the intensity of the near-infrared autofluorescence, transmissivity needs to be appropriately reduced and a detailed filter design will be described through FIG. 7 below.

FIG. 7 illustrates a design of the autofluorescence and visible light emission filter 220A adjusting an optical density (OD) spectrum according to an embodiment of the present invention.

The autofluorescence and visible light emission filter 220A according to an embodiment of the present invention may be designed so that the visible light region has an OD of approximately 2 (region a), an OD of 6 or more around a light source wavelength so as to prevent light source light having a wavelength of 780 nm from being input (region b), and an OD value of 0 around 832 nm which is an autofluorescence wavelength (region c).

Here, region a is the visible light region, region b is an excitation wavelength region in the near-infrared region, and region c is an emission wavelength region in the near-infrared region. When the autofluorescence and visible light emission filter 220A is designed as illustrated in FIG. 7, the OD value of region a is designed to approximately 2 and the OD value of region c is designed to 0, and as a result, a transmissivity ration between the visible light region and the emission wavelength region becomes approximately 0.01:1.

In this case, the transmissivity of an emission wavelength (region c) is preferably designed to be higher than that of the visible light region (region a) and a difference in transmissivity ratio or OD value between region a and region c may be approximately adjusted according to the intensity of the visible light lighting of the operating room and the intensity of the emitted autofluorescence. Preferably, the transmissivity ratio may be designed to 0.01 to 0.0001:1.

Region b as a region of the excitation wavelength in the near-infrared region should be designed so that the transmissivity is extremely low in order to block the light of the light source 100. The OD of the excitation wavelength may be preferably designed to be 6 or more.

Meanwhile, the transmissivity ratio between the visible light region and the emission wavelength region and the transmissivity of the excitation wavelength may be appropriately adjusted according to an individual difference of a surgeon and an environment of the operating room. Further, a filter may be used, which automatically adjusts the OD value electrically or by other schemes.

Mode for Invention

Terms or words used in the present specification and claims should not be interpreted as being limited to typical or dictionary meanings, but should be interpreted as having meanings and concepts which comply with the technical spirit of the present disclosure, based on the principle that an inventor can appropriately define the concept of the term to describe his/her own invention in the best manner. Accordingly, configurations illustrated in the exemplary embodiments and drawings disclosed in the present specification are only the most preferred embodiment of the present invention and do not represent all of the technical spirit of the present invention, and thus it is to be understood that various equivalents and modified examples, which may replace the configurations, are possible when filing the present application. Hereinafter, a real-time parathyroid imaging system according to an embodiment of the present invention will be described in detail with reference to the accompanying drawings.

Figure 1:
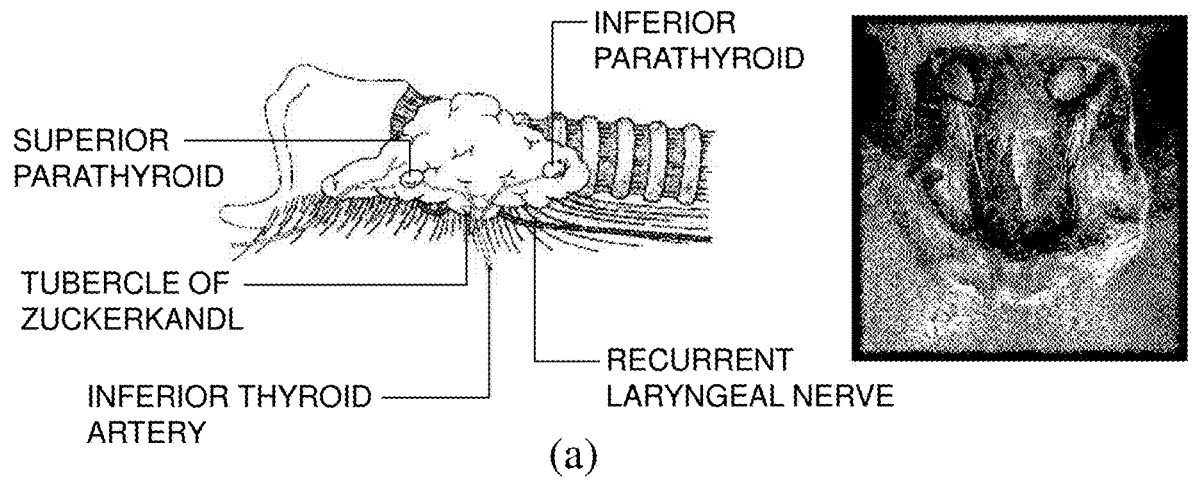
FIG. 1(a) illustrates a location of parathyroid and FIG. 1(b) illustrates subgroups of lymph glands.
Figure 1:
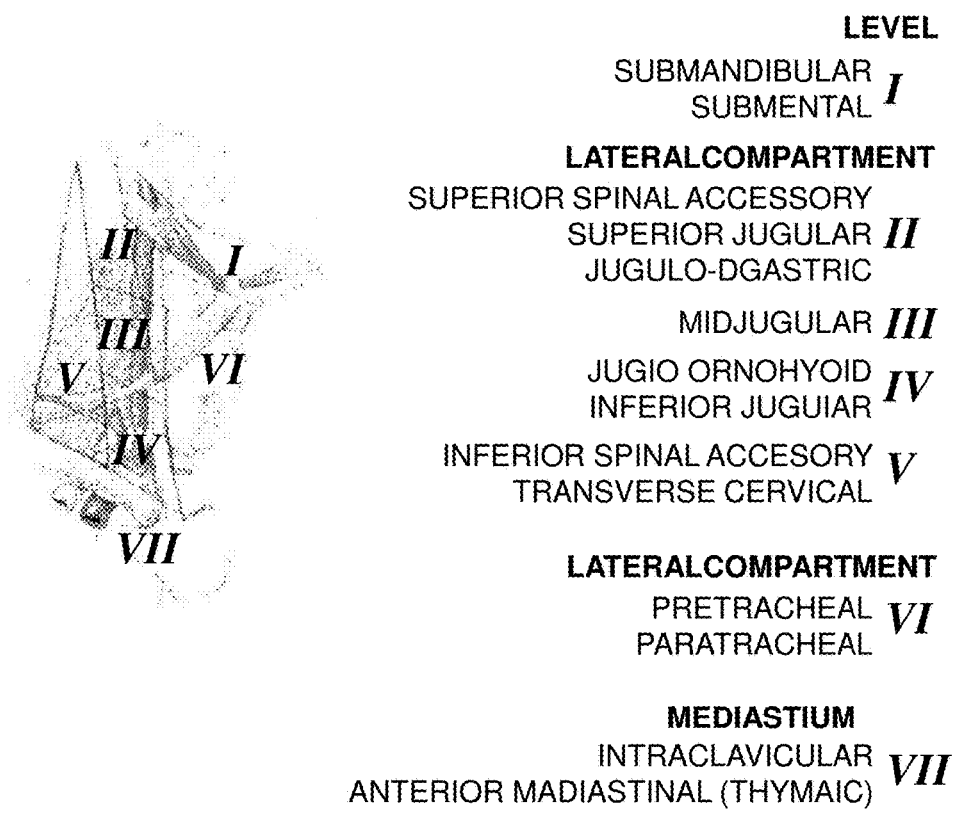
Figure 2:
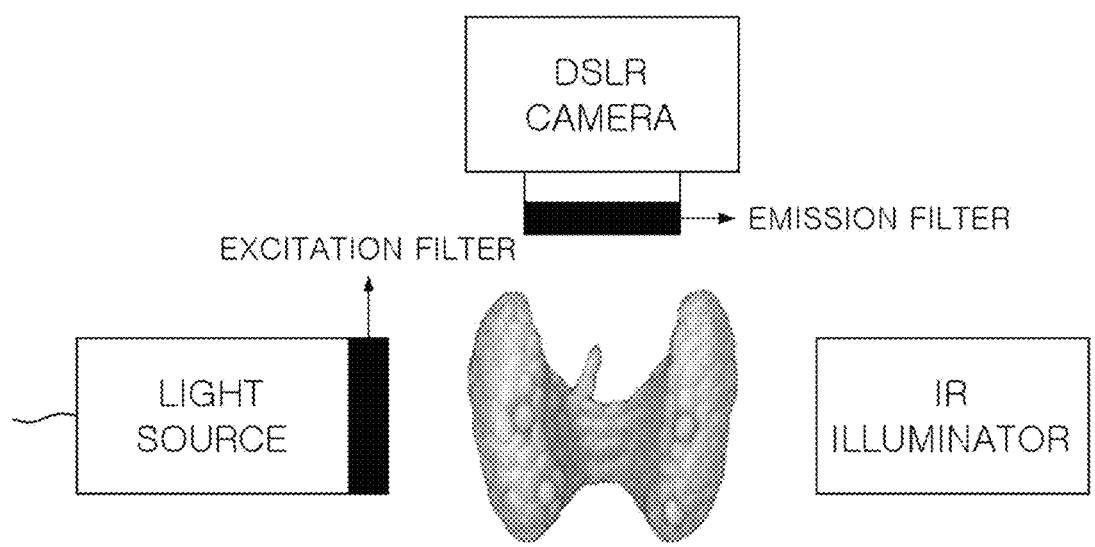
FIG. 2 illustrates a conventional parathyroid imaging system.
Figure 3:
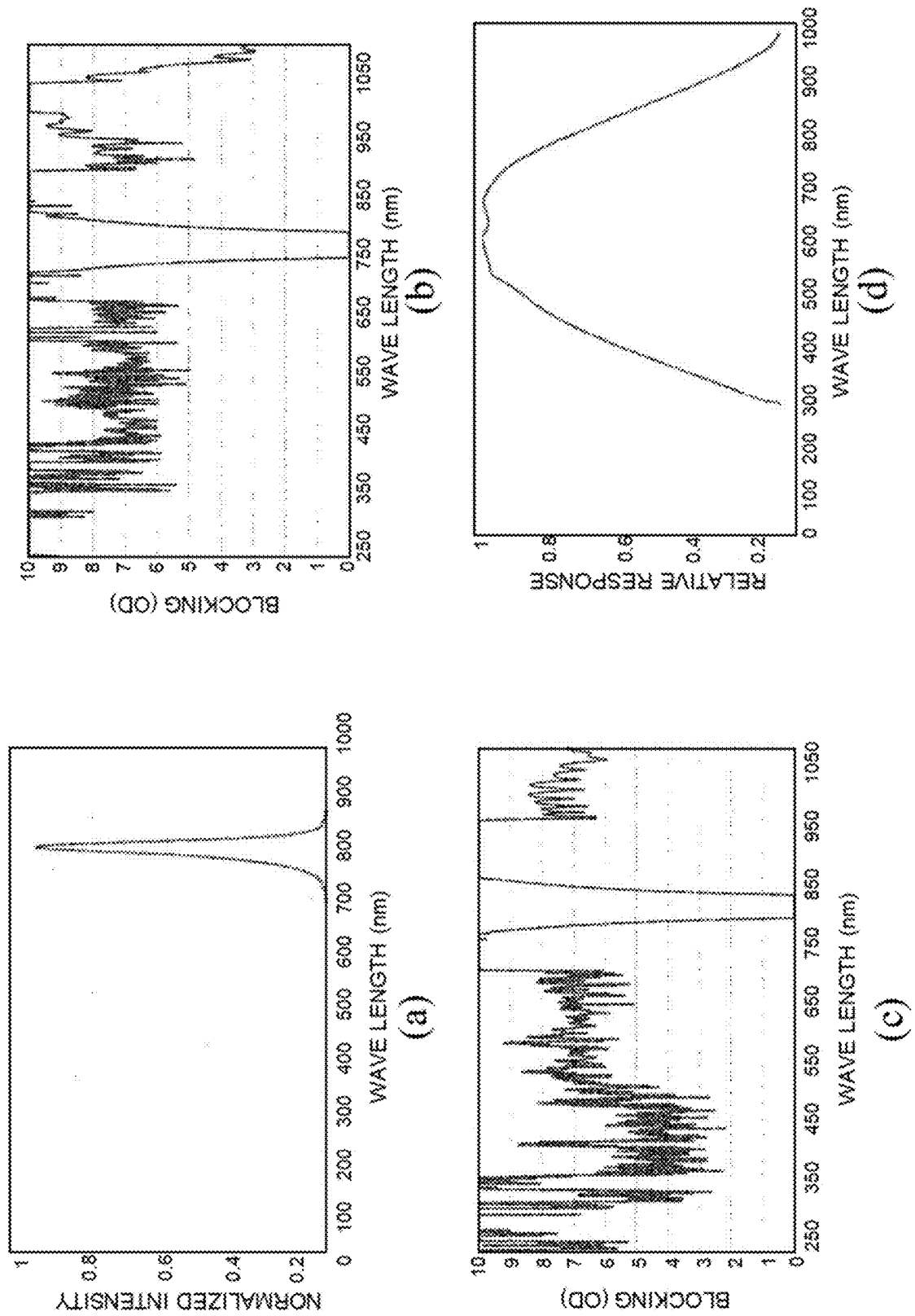
FIG. 3(a) is a spectrum graph of an LED light source in which a center wavelength is 780 nm.
FIG. 3(b) is a spectrum graph of an excitation filter having a center wavelength of 769 mm and a bandwidth of 41 nm.
FIG. 3(c) is a spectrum graph of an emission filter having a center wavelength of 832 mm and a bandwidth of 37 nm.
FIG. 3(d) is a graph showing sensitivity depending on a wavelength of a camera sensor which is a detector, in the conventional parathyroid imaging system according to FIG. 2.
Figure 4:
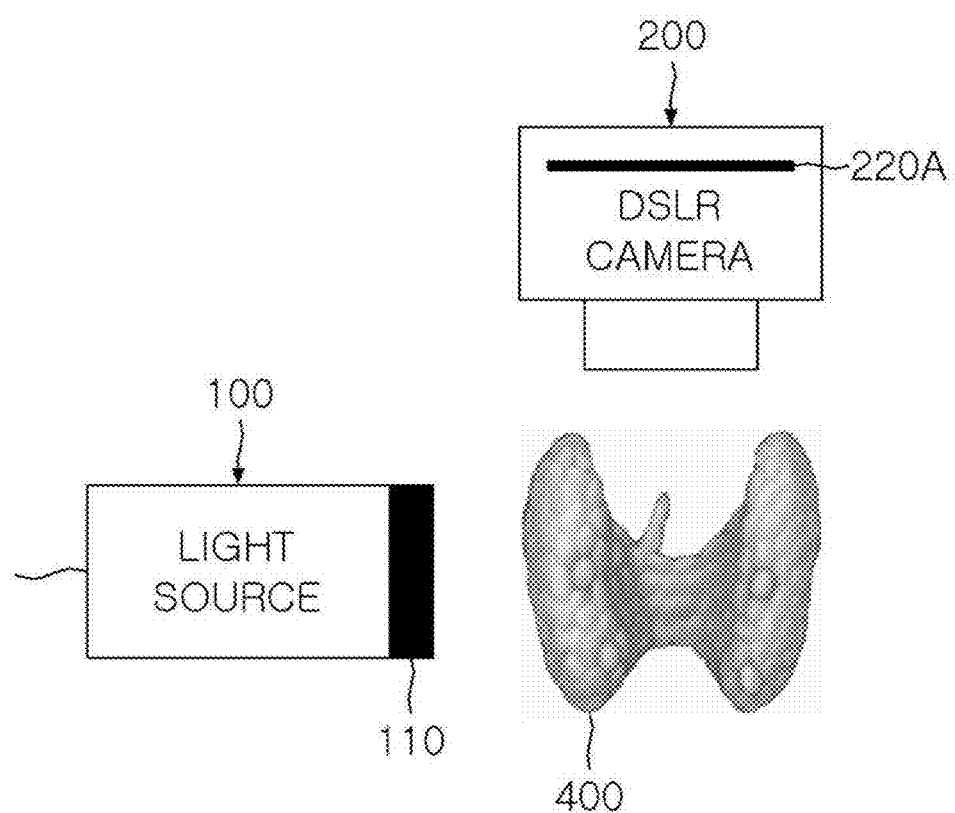
FIG. 4 illustrates a configuration of a real-time parathyroid imaging system according to the present invention.

FIG. 4 illustrates a configuration of a real-time parathyroid imaging system according to the present invention.

Since the parathyroid has a particular excitation spectrum and a particular emission spectrum, there should be a light source and a camera suitable therefor. In this case, since the excitation spectrum and the emission spectrum generally overlap with each other, an excitation filter and an emission filter should be used.

The real-time parathyroid imaging system according to the present invention includes a light source 100 capable of exciting parathyroid and a camera (or detector 200) capable of detecting autofluorescence emitted by the parathyroid. An excitation filter 110 may be included in the light source 100 and a particular emission filter 220A may be included in the camera. The emission filter which becomes a core of the present invention will be described in detail in parts for describing FIGS. 6 and 7.

Figure 5:
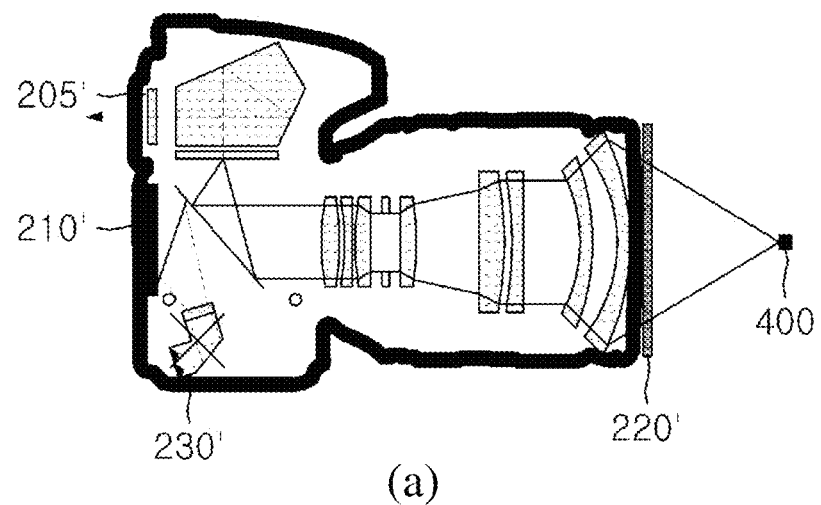
FIG. 5(a) illustrates a conventional DSLR camera structure and FIG. 5(b) illustrates a DSLR camera structure according to the present invention.
Figure 5:
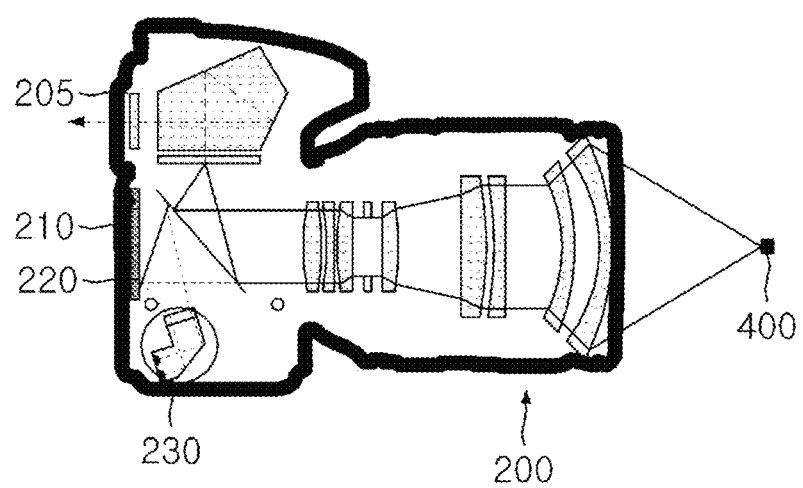

FIG. 5(*a*) illustrates a conventional DSLR camera structure and FIG. 5(*b*) illustrates a DSLR camera structure according to the present invention.

In the related art, as illustrated in FIG. 5(*a*), a DSLR infrared filter immediately in front of an image sensor 210' is removed, a glass plate is inserted into a portion where the DSLR infrared filter is removed, and an infrared emission filter 220' is installed in front of a lens.

In such a structure, the same parathyroid near-infrared autofluorescence image is input into the image sensor 210' and a viewfinder 205' and in this case, since the amount of light is very insufficient, an auto focus device 230' does not operate, and as a result, there is inconvenience that a focus should be adjusted manually. Further, since the autofluorescence image is not viewed even in the viewfinder 205' due to an insufficient light amount and invisible nature of infrared light, the focus should be manually adjusted in a blind situation.

On the contrary, the present invention has a structure in which the infrared emission filter 220 is located adjacent immediately in front of the image sensor 210 as illustrated in FIG. 5(*b*). An autofocusing function may be performed through such a structure.

In a camera structure according to the present invention, since the autofluorescence image is recognized by the image sensor 210 and the visible light image is recognized by the viewfinder 205, a photographer using the viewfinder 205 easily focuses on the parathyroid and the auto focus device 230 also senses visible light having a sufficient light amount, and as a result, the auto focus device 230 may smoothly operate.

Meanwhile, in order to reduce background noise of the autofluorescence, the light in the operating room is recommended to be turned off, but the light is preferred to be turned on for convenience of the surgeon, and as a result, the background noise needs to be maximally reduced at the time of turning on a fluorescent lamp in the operating room.

As a result of measuring the spectrum of the fluorescent lamp in the operating room, it is confirmed that a small amount of light passing through the infrared emission filter 220 is emitted. Accordingly, it is necessary to appropriately adjust the bandwidth of the infrared emission filter 220 and the optical density (OD) in the visible light region.

FIG. 6 illustrates a DSLR camera structure with an autofluorescence and visible light emission filter 220A according to the present invention and FIG. 7 is a graph showing an optical density (OD) depending on wavelength of the emission filter 220A according to an embodiment of the present invention.

Only a near-infrared autofluorescence image of the parathyroid may be acquired through the camera illustrated in FIG. 5(*a*) or 5(*b*). When using near-infrared illuminator in addition to an excitation light source, it is possible to image not only the parathyroid but also a periphery thereof, but when only the image of the near-infrared region is acquired, it is inconvenient for a surgeon to recognize the location of the parathyroid during an operation due to a significant difference from the image in the visible light region recognized by a person.

In the present invention, in order to supplement the inconvenience, an autofluorescence and visible light emission filter 220A is introduced in the camera, which enables the location of the parathyroid to be recognized in a surrounding structure in an operation room by fusing a near-infrared autofluorescence image and a visible light image into one image.

In FIG. 6, as the camera according to the present invention, a camera can be seen, which includes the autofluorescence and visible light emission filter 220A for acquiring a fused image in addition to an auto focus function.

A transmission spectrum of the autofluorescence and visible light emission filter 220A is adjusted to allow the visible light to pass with a similar intensity as the near-infrared autofluorescence and the autofluorescence and visible light emission filter 220A is installed adjacent immediately in front of the image sensor 210. Since the intensity of the visible light is stronger than the intensity of the near-infrared autofluorescence, transmissivity needs to be appropriately reduced and a detailed filter design will be described through FIG. 7 below.

FIG. 7 illustrates a design of the autofluorescence and visible light emission filter 220A adjusting an optical density (OD) spectrum according to an embodiment of the present invention.

The autofluorescence and visible light emission filter 220A according to an embodiment of the present invention may be designed so that the visible light region has an OD of approximately 2 (region a), an OD of 6 or more around a light source wavelength so as to prevent light source light having a wavelength of 780 nm from being input (region b), and an OD value of 0 around 832 nm which is an autofluorescence wavelength (region c).

Here, region a is the visible light region, region b is an excitation wavelength region in the near-infrared region, and region c is an emission wavelength region in the near-infrared region. When the autofluorescence and visible light emission filter 220A is designed as illustrated in FIG. 7, the OD value of region a is designed to approximately 2 and the OD value of region c is designed to 0, and as a result, a transmissivity ratio between the visible light region and the emission wavelength region becomes approximately 0.01:1.

In this case, the transmissivity of an emission wavelength (region c) is preferably designed to be higher than that of the visible light region (region a) and a difference in transmissivity ratio or OD value between region a and region c may be approximately adjusted according to the intensity of the visible light lighting of the operating room and the intensity of the emitted autofluorescence. Preferably, the transmissivity ratio may be designed to 0.01 to 0.0001:1.

Region b as a region of the excitation wavelength in the near-infrared region should be designed so that the transmissivity is extremely low in order to block the light of the light source 100. The OD of the excitation wavelength may be preferably designed to 6 or more.

Meanwhile, the transmissivity ratio between the visible light region and the emission wavelength region and the transmissivity of the excitation wavelength may be appropriately adjusted according to an individual difference of a surgeon and an environment of the operating room. Further, a filter may be used, which automatically adjusts the OD value electrically or by other schemes.

Figure 8:
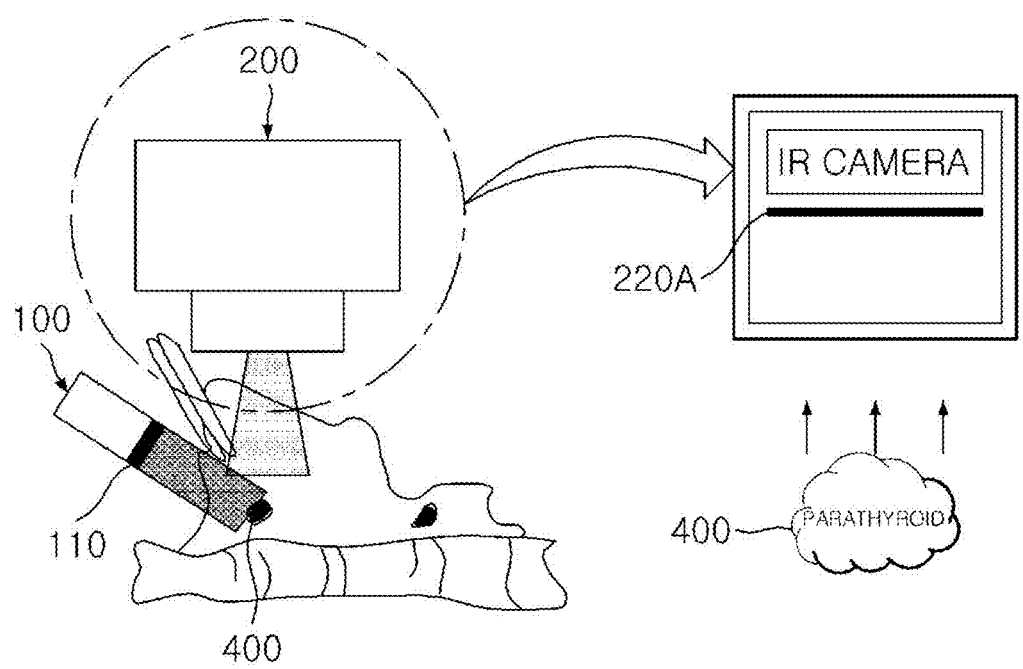
FIG. 8 schematically illustrates a process of acquiring an image in which real-time autofluorescence and visible light are fused by using a small-sized IR camera having increased sensitivity in near-infrared rays including an emission filter 220A according to the present invention.

FIG. 8 schematically illustrates a process of acquiring an image in which real-time autofluorescence and visible light are fused by using a small-sized IR camera having increased sensitivity in near-infrared rays including an emission filter 220A according to the present invention.

In order to acquire the parathyroid autofluorescence with a real-time moving picture, an IR dedicated camera having high sensitivity in near-infrared rays may be used, but this is very expensive, and as a result, in the present invention, a camera for a cellular phone is used, which is low-priced and small-sized in addition to the IR dedicated camera.

As described above, when the parathyroid and the vicinity thereof are imaged together, if only an image of the near-infrared region is acquired, there is inconvenience for the surgeon to recognize the location of the parathyroid during surgery. Therefore, in the related art, in order to solve the inconvenience, a scheme is adopted in which a camera is additionally installed, which acquires the visible light image to acquire two images and fuse the acquired images.

However, when the autofluorescence and visible light emission filter 220A according to the present invention is used, a complex multi-channel system using multiple cameras may be implemented through one camera.

Figure 9:
FIG. 9(a) illustrates a visible light image.
FIG. 9(b) illustrates a near-infrared autofluorescence image.
FIG. 9(c) illustrates an image acquired by fusing both images of FIG. 9(a) and FIG. 9(b), as images acquired by photographing parathyroid through the system of FIG. 8.
Figure 9:
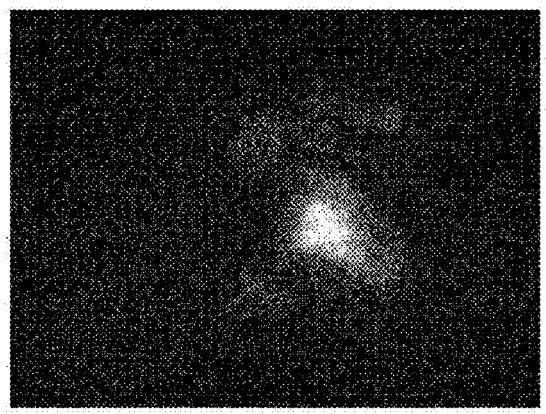
Figure 9:

FIG. 9(*a*) illustrates a visible light image, FIG. 9(*b*) illustrates a near-infrared autofluorescence image, and FIG. 9(*c*) illustrates an image acquired by fusing both images of FIG. 9(*a*) and FIG. 9(*b*), as images acquired by photographing parathyroid through the system of FIG. 8.

The surgeon may not easily identify the parathyroid only with the visible image which is the image illustrated in FIG. 9(*a*). There is a sense of heterogeneity from the visible light region actually recognized by the person with only the image of the near-infrared parathyroid autofluorescence which is the image illustrated in FIG. 9(*b*) and since there is no surrounding image of the parathyroid, the surgeon does not easily identify the location of the parathyroid during the operation.

Accordingly, it is necessary to acquire the image illustrated in FIG. 9(*c*), i.e., the image acquired by fusing both images. In the present invention, the autofluorescence and visible light emission filter 220A is introduced and implemented. The surgeon may more clearly determine the location of the parathyroid through the image illustrated in FIG. 9(*c*).

Although representative exemplary embodiments of the present invention have been described in detail hereinabove, it will be appreciated by those skilled that various modifications of the exemplary embodiment of the present invention can be made in the art within a limit without departing from the scope of the present invention. Therefore, the scope of the present invention should not be limited to the embodiments and should be defined by the appended claims and equivalents to the appended claims.

What is claimed is:

1. A parathyroid imaging system comprising:
   a light source including an excitation filter for exciting parathyroid glands; and
   a camera including an emission filter of which a transmissivity ratio between a visible light region and a near-infrared emission wavelength region is N:1 where N is less than one, and an image sensor,
   wherein the emission filter is configured to include a first optical density (OD) region that is the visible light region, a second OD region that is a near-infrared excitation wavelength region, and a third OD region that is the near-infrared emission wavelength region,
   an OD value of the second OD region is greater than that of the first OD region in order to block the light of the light source, and
   the OD value of the first OD region is greater than that of the third OD region so that transmissivity of the near-infrared emission wavelength region is higher than that of the visible light region, and
   wherein said parathyroid imaging system is configured to simultaneously provide an autofluorescence image of said parathyroid glands' location and a visible light image of a surrounding tissue location that does not overlap with said parathyroid glands, from images obtained by said camera, and thereby to make it possible to easily identify a location of said parathyroid glands by said autofluorescence image through assistance of said visible light image of said surrounding tissue.

2. The parathyroid imaging system of claim 1, wherein the N is in the range of 0.01 to 0.0001.

3. The parathyroid imaging system of claim 1, wherein the OD value of the second OD region is 6 or more.

4. The parathyroid imaging system of claim 1, wherein the emission filter is positioned adjacent to the image sensor.

* * * * *